United States Patent
De Jongh et al.

(10) Patent No.: US 12,383,396 B2
(45) Date of Patent: Aug. 12, 2025

(54) EXPANDABLE SLEEVED STENT AND METHOD OF MAKING SUCH STENT

(71) Applicant: Strait Access Technologies Holdings (PTY) LTD, Cape Town (ZA)

(72) Inventors: Bruce De Jongh, Hout Bay (ZA); Deon Bezuidenhout, Cape Town (ZA); Peter Zilla, Cape Town (ZA); Carel Sebastiaan Van Heerden, Meadowridge (ZA); Johan Coetzee, Newlands (ZA)

(73) Assignee: STRAIT ACCESS TECHNOLOGIES HOLDINGS (PTY) LTD, Cape Town (ZA)

( * ) Notice: Subject to any disclaimer, the term of this patent is extended or adjusted under 35 U.S.C. 154(b) by 525 days.

(21) Appl. No.: 17/269,301

(22) PCT Filed: Aug. 23, 2019

(86) PCT No.: PCT/ZA2019/050052
§ 371 (c)(1),
(2) Date: Feb. 18, 2021

(87) PCT Pub. No.: WO2020/056435
PCT Pub. Date: Mar. 19, 2020

(65) Prior Publication Data
US 2021/0212820 A1 Jul. 15, 2021

(30) Foreign Application Priority Data
Sep. 11, 2018 (GB) .................................. 1814734

(51) Int. Cl.
*A61F 2/24* (2006.01)
*A61F 2/91* (2013.01)
*A61F 2/95* (2013.01)

(52) U.S. Cl.
CPC .......... *A61F 2/2418* (2013.01); *A61F 2/2415* (2013.01); *A61F 2/91* (2013.01); *A61F 2/9522* (2020.05); *A61F 2240/001* (2013.01)

(58) Field of Classification Search
CPC ...................................................... A61F 2/2418
See application file for complete search history.

(56) References Cited

U.S. PATENT DOCUMENTS 5,330,528 A    7/1994   Lazim
5,449,385 A * 9/1995   Religa .................. A61F 2/2412
                                                    623/2.19
(Continued)

FOREIGN PATENT DOCUMENTS

DE    102014102653    9/2015
EP    2749254    7/2014
(Continued)

OTHER PUBLICATIONS

International search report and written opinion dated Oct. 30, 2019 in international patent application No. PCT/ZA2019/050052.

*Primary Examiner* — Jacqueline Woznicki
(74) *Attorney, Agent, or Firm* — Billion & Armitage (57) ABSTRACT

An expandable sleeved stent comprises a stent and a sleeve. The stent comprises a tubular body with: first and second axial ends; a latticed peripheral wall; and at least two arms that, upon radial expansion of the tubular body from a crimped condition to an expanded condition, protrude radially from the latticed peripheral wall, the free end of each arm being radially displaceable relative to the adjacent latticed peripheral wall. The sleeve: (a) extends from the first axial end of the tubular body and circumferentially covers at least a portion of the radial outer surface of the latticed peripheral wall between the free ends of the arms and the first axial end of the tubular body; (b) bridges the spaces between the portions of the latticed peripheral wall adjacent (Continued)

the arms; and the free ends of the arms; and (c) is secured to either: (i) the arms; or (ii) the tubular body in the vicinity between the free ends of the arms and the second axial end of the tubular body. Upon radial expansion of the tubular body towards the expanded condition and consequent protrusion of the arms radially from the latticed peripheral wall, the portions of the sleeve that bridge the latticed peripheral wall and the arms flare radially outwards.

7 Claims, 7 Drawing Sheets

(56) References Cited

U.S. PATENT DOCUMENTS

| | | | | |
|---|---|---|---|---|
| 5,549,665 | A * | 8/1996 | Vesely | A61F 2/2409 623/2.14 |
| 5,665,117 | A | 9/1997 | Rhodes | |
| 5,693,088 | A | 12/1997 | Lazarus | |
| 7,044,962 | B2 | 5/2006 | Elliott | |
| 7,445,642 | B2 | 11/2008 | Amos et al. | |
| 7,803,178 | B2 | 9/2010 | Whirley | |
| 10,456,245 | B2 * | 10/2019 | Nguyen | A61L 31/10 |
| 10,631,978 | B2 * | 4/2020 | Park | A61F 2/2406 |
| 2001/0021872 | A1 * | 9/2001 | Bailey | A61F 2/2469 623/2.18 |
| 2002/0169497 | A1 | 11/2002 | Wholey et al. | |
| 2003/0028244 | A1 * | 2/2003 | Bates | A61L 31/16 623/1.42 |
| 2004/0044358 | A1 | 3/2004 | Khosravi et al. | |
| 2004/0082989 | A1 | 4/2004 | Cook et al. | |
| 2004/0098096 | A1 | 5/2004 | Eton | |
| 2004/0176836 | A1 | 9/2004 | Kari et al. | |
| 2005/0137692 | A1 * | 6/2005 | Haug | A61F 2/2439 623/2.11 |
| 2005/0137699 | A1 * | 6/2005 | Salahieh | A61F 2/2418 623/2.11 |
| 2005/0228484 | A1 | 10/2005 | Stephens et al. | |
| 2006/0025853 | A1 | 2/2006 | Evans et al. | |
| 2006/0271172 | A1 | 11/2006 | Tehrani | |
| 2006/0292206 | A1 | 12/2006 | Kim et al. | |
| 2008/0058920 | A1 | 3/2008 | Kari | |
| 2008/0082166 | A1 * | 4/2008 | Styrc | A61F 2/2418 623/2.18 |
| 2008/0234809 | A1 | 9/2008 | Greenan | |
| 2008/0255661 | A1 * | 10/2008 | Straubinger | A61F 2/2427 623/2.36 |
| 2009/0112305 | A1 | 4/2009 | Goldmann et al. | |
| 2010/0070027 | A1 * | 3/2010 | Bonhoeffer | A61F 2/2436 623/2.11 |
| 2011/0295363 | A1 * | 12/2011 | Girard | A61F 2/2412 623/1.26 |
| 2012/0165917 | A1 | 6/2012 | Schreck et al. | |
| 2012/0316656 | A1 | 12/2012 | Deal et al. | |
| 2013/0274873 | A1 * | 10/2013 | Delaloye | A61F 2/2469 623/2.18 |
| 2013/0304200 | A1 | 11/2013 | Mclean et al. | |
| 2014/0018915 | A1 * | 1/2014 | Biadillah | A61F 2/2418 623/2.17 |
| 2014/0058436 | A1 | 2/2014 | Rosenbluth et al. | |
| 2014/0222136 | A1 | 8/2014 | Geist et al. | |
| 2014/0296975 | A1 | 10/2014 | Tegels et al. | |
| 2014/0358216 | A1 | 12/2014 | Schreck et al. | |
| 2015/0142103 | A1 | 5/2015 | Vidlund | |
| 2015/0148894 | A1 * | 5/2015 | Damm | A61F 2/2436 623/2.11 |
| 2015/0289973 | A1 * | 10/2015 | Braido | A61F 2/2412 623/2.17 |
| 2016/0038280 | A1 | 2/2016 | Morriss et al. | |
| 2016/0213465 | A1 * | 7/2016 | Girard | A61F 2/2409 |
| 2016/0220366 | A1 * | 8/2016 | Burriesci | A61F 2/2418 |
| 2016/0338823 | A1 | 11/2016 | Akingba | |
| 2017/0071734 | A1 | 3/2017 | Delaloye et al. | |
| 2018/0147061 | A1 * | 5/2018 | Drasler | A61F 2/2412 |
| 2018/0206982 | A1 * | 7/2018 | Haivatov | A61F 2/2418 |
| 2018/0221146 | A1 | 8/2018 | Jana et al. | |
| 2018/0289476 | A1 * | 10/2018 | Vyas | A61F 2/2418 |
| 2018/0303612 | A1 * | 10/2018 | Pasquino | A61F 2/2448 |
| 2019/0099266 | A1 * | 4/2019 | Nelson | A61F 2/2418 |
| 2019/0336283 | A1 * | 11/2019 | Le Cerf | A61F 2/2418 |
| 2020/0163760 | A1 * | 5/2020 | Hariton | A61F 2/2418 |
| 2020/0306037 | A1 * | 10/2020 | Siegel | A61M 25/0045 264/269 |
| 2021/0145572 | A1 * | 5/2021 | Dasi | A61L 27/20 |
| 2021/0212820 | A1 * | 7/2021 | De Jongh | A61F 2/2415 |
| 2022/0192824 | A1 * | 6/2022 | Vidlund | A61F 2/2418 |

FOREIGN PATENT DOCUMENTS

| | | |
|---|---|---|
| EP | 2815723 | 12/2014 |
| EP | 2926766 | 10/2015 |
| WO | 9528899 | 11/1995 |
| WO | 2007098937 | 9/2007 |
| WO | 2010008548 | 1/2010 |
| WO | 2016073189 | 5/2016 |
| WO | 2017081679 | 5/2017 |
| WO | 2017101232 | 6/2017 |
| WO | 2017163247 | 9/2017 |
| WO | 2017190161 | 11/2017 |

* cited by examiner

EXPANDABLE SLEEVED STENT AND METHOD OF MAKING SUCH STENT

BACKGROUND

The present invention relates to an expandable sleeved stent. More particularly, the present invention relates to an expandable sleeved stent including: (i) a tubular body comprising a latticed peripheral wall and arms that protrude radially from the latticed peripheral wall upon radial expansion of the tubular body; and (ii) a sleeve that extends circumferentially along a portion of both the latticed peripheral wall and the arms. Even more particularly, the present invention relates to an expandable sleeved stent including radially extendable arms and a sleeve, wherein the sleeve bridges the free ends of the arms and adjacent portions of the latticed peripheral wall, such that, upon protrusion of the arms radially from the latticed peripheral wall, the bridging portions of the sleeve flare radially. The present invention also relates to an expandable sleeved stent, wherein the sleeve defines radially outwards extending humps for receiving radially protruding stent arms therein upon radial expansion of the stent. Furthermore, the present invention relates to a method of making an expandable sleeved stent.

Stents are used to treat aneurysms and to anchor and support replacement valves. When secured in a patient's vascular system, the radial outer surface of the stent is preferably sealed against the wall of the vascular system. Failure to create such seal permits blood flow between the radial outer surface of the stent and the wall of the vascular system, which in turn may apply pressure to the aneurism or cause paravalvular leakage. To improve the seal between the stent and the wall of the vascular system, various bladders, sleeves, skirts or formations have been added to stents, which added features protrude radially beyond the radial outer surface of the stent. For instance:

US2006/0271172 "Minimally invasive aortic valve replacement" describes a stent with deformable rings on the radial outer surface of the stent.

US2006/0292206 "Devices and methods for treatment of vascular aneurysms" and EP2815723 "Collapsible and re-expandable prosthetic heart valve cuff designs and complementary technological applications" describe a stent with an expandable material on the radial outer surface of the stent.

US2009/0112305 "Stent-graft prosthesis" and US2014/0058436 "Blood flow disruption devices and methods for the treatment of vascular defects" describe a stent with a radially expandable sleeve about the radial outer surface of the stent.

US2004/0044358 "Methods and apparatus for treating aneurysms and arterio-venous fistulas", US2004/0098096 "Endograft device to inhibit endoleak and migration", US2004/0176836 "Kink resistant endovascular graft", US2005/0228484 "Modular endovascular graft", US2006/0025853 "Methods and systems for endovascular aneurysm treatment", US2008/0058920 "Dual chamber cuff structure", US2008/0234809 "Stent graft system with injection tube", US2012/0316656 "Balloon expandable stent", US2012/0165917 "Stent graft", US2014/358216 "Stent graft", U.S. Pat. No. 5,330,528 "Vascular surgical devices", U.S. Pat. No. 5,665,117 "Endovascular prosthesis with improved sealing means for aneurysmal arterial disease and method of use", U.S. Pat. No. 5,693,088 "Intraluminal vascular graft", U.S. Pat. No. 7,445,642 "Agent eluting stent and catheter", U.S. Pat. No. 7,803,178 "Inflatable porous implants and methods for drug delivery" and WO95/28899 "Stented bioprosthetic heart valve" describe a stent (or other carrier) including a double-walled bladder that is inflated to expand radially from the radial outer surface of the stent by the introduction of fluid (e.g. blood) between the bladder walls.

EP2926766 "Repositionable heart valve" describes a stent with inflatable sacs on the radial outer surface of the stent.

US2014/0296975 "Inflatable annular sealing device for prosthetic mitral valve" describes a stent with a skirt and a shell that expands from the radial outer surface of the stent.

US2002/0169497 "Endovascular stent system and method of providing aneurysm embolization", US2004/0082989 "Stent graft with improved proximal end", WO2016/073189 "Transcatheter valve prosthesis having an external skirt for sealing and preventing paravalvular leakage" and EP2749254 "Repositionable heart valve" describe a stent with a sleeve circumferentially covering a portion of the stent.

U.S. Pat. No. 7,044,962 "Implantable prosthesis with displaceable skirt" describes a stent including a skirt on the radial outer surface of the stent, the skirt having a free peripheral edge that can be deployed into a flared condition.

US2015/0142103 "Multi-component designs for heart valve retrieval device, sealing structures and stent assembly", US2016/0338823 "Jaxtarenal stent and methods", US2017/0071734 "Transcatheter stent-valves and methods, systems and devices for addressing para-valve leakage", WO2017/081679 "Stent-grafts systems with skirt" and WO2017/101232 "Artificial heart valve stent, artificial heart valve and implantation method" describe: (i) a stent having a peripheral wall and arms that extend radially from the peripheral wall; and (ii) a sleeve that extends over a portion of the peripheral wall and that radiates along the stent arms to form a skirt. In each instance, the skirt extends from the peripheral wall and along the stent arms from the hinged connection of the stent arms to the peripheral wall to the free ends of the stent arms. Neither the sleeve, nor the skirt bridges the gap between the free ends of the stent arms and the peripheral wall.

An object of the present invention is to provide a sleeved stent, wherein radial expansion of the stent causes the sleeve to expand radially and form (in axial cross-section) a cylindrical sleeve with at least two humps supported by radially extending stent arms.

SUMMARY OF THE INVENTION

According to a first aspect of the invention, there is provided an expandable sleeved stent that comprises:
  a tubular body with: first and second axial ends; a latticed peripheral wall; and at least two arms that, upon radial expansion of the tubular body from a crimped condition to an expanded condition, protrude radially from the latticed peripheral wall, the free end of each arm being radially displaceable relative to the adjacent latticed peripheral wall;
  a sleeve that:
    extends from the first axial end of the tubular body and circumferentially covers at least a portion of the radial outer surface of the latticed peripheral wall between the free ends of the arms and the first axial end of the tubular body;
    bridges the spaces between: the portions of the latticed peripheral wall adjacent the arms; and the free ends of the arms; and
    is secured to either: (i) the arms; or (ii) the tubular body in the vicinity between the free ends of the arms and the second axial end of the tubular body, such that, upon radial expansion of the tubular body towards the expanded condition and consequent protrusion of the arms radially from the latticed peripheral wall, the portions of the sleeve that bridge the latticed peripheral wall and the arms flare radially outwards.

Typically, when the tubular body is in the crimped condition, the sleeve: (i) in the region that radially overlaps the latticed peripheral wall is right circular cylindrical in shape; and (ii) in the regions that radially overly the arms define radially outward extending humps.

Generally, when the tubular body is in the crimped condition, the humps defined by the sleeve provide pockets between the sleeve and associated arms, into which pockets the arms may extend upon radial expansion of the tubular body towards the expanded condition.

Preferably:
each arm includes: (i) a first arm lattice member; (ii) a generally U-shaped second arm lattice member; and (iii) a third arm lattice member bridging the first and second arm lattice members; and
the sleeve extends to, and is secured to the first arm lattice member of each arm.

Typically, in respect of each arm, the second arm lattice member is not secured to the sleeve, permitting sliding movement of the second arm lattice member along the sleeve in the region of the corresponding hump defined by the sleeve upon radial expansion of the tubular body towards the expanded condition.

Generally, the sleeve is made of an electrospun polymer.

Preferably, each hump defined by the sleeve is kidney-shaped, curving between the axial ends of the second arm lattice member.

Typically, the tubular body is coated in a polymer and the sleeve is bonded to the tubular body.

Optionally, the tubular body is bonded to scalloped members forming part of the latticed peripheral wall adjacent the second arm lattice members.

Generally: the tubular body includes three arms; and the sleeve defines three humps.

Preferably: a first portion of the sleeve is made of single layered polymer material; and second portions of the sleeve are made of double-layered polymer material.

According to a second aspect of the invention, there is provided an expandable sleeved stent that comprises:
a tubular body with: first and second axial ends; a latticed peripheral wall; and at least two arms that, upon radial expansion of the tubular body from a crimped condition to an expanded condition, protrude radially from the latticed peripheral wall, the free end of each arm being radially displaceable relative to the adjacent latticed peripheral wall; and
a sleeve that:
  extends from the first axial end of the tubular body and circumferentially covers at least a portion of the radial outer surface of the latticed peripheral wall between the free ends of the arms and the first axial end of the tubular body;
  bridges the spaces between the portions of the latticed peripheral wall adjacent the arms; and the free ends of the arms;
  covers the arms; and
  when the tubular body is in the crimped condition:
    in the region of the sleeve that radially overlaps the latticed peripheral wall, is right circular cylindrical in shape; and
    in the regions of the sleeve that radially overly the arms, define radially outward extending humps, providing pockets between the sleeve and associated arms,
such that, upon protrusion of the arms radially from the latticed peripheral wall, the arms extend into the pockets provided by the humps.

Typically, in respect of each arm, the free end of the arm is not secured to the sleeve, permitting sliding movement of the free end of the arm along the sleeve in the region of the corresponding hump defined by the sleeve upon radial expansion of the tubular body towards the expanded condition.

Generally: the tubular body includes three arms; and the sleeve defines three humps.

According to a third aspect of the invention, there is provided a method of making an expandable sleeved stent, including the steps of:
providing an expandable stent comprising a tubular body with: first and second axial ends; a latticed peripheral wall; and at least two arms that, upon radial expansion of the tubular body from a crimped condition to an expanded condition, protrude radially from the latticed peripheral wall, the free end of each arm being radially displaceable relative to the adjacent latticed peripheral wall;
electrospinning a polymer onto a first cylindrical mandrel to create a sleeve;
stretching the sleeve over a second cylindrical mandrel that defines at least two radially outward extending humps symmetrically spaced about the second cylindrical mandrel;
heating the sleeve to cause the sleeve to assume the shape of the second cylindrical mandrel with humps; and
placing the sleeve over the stent, with the humps formed in the sleeve radially overlying the stent arms.

BRIEF DESCRIPTION OF THE DRAWINGS

The invention will now be described in more detail, by way of example only, with reference to the accompanying drawings in which.

DESCRIPTION OF THE INVENTION

With reference to FIGS. 1 to 5 of the drawings, an expandable sleeved stent 10 includes a stent 12 and a sleeve 14.

Figure 4A:
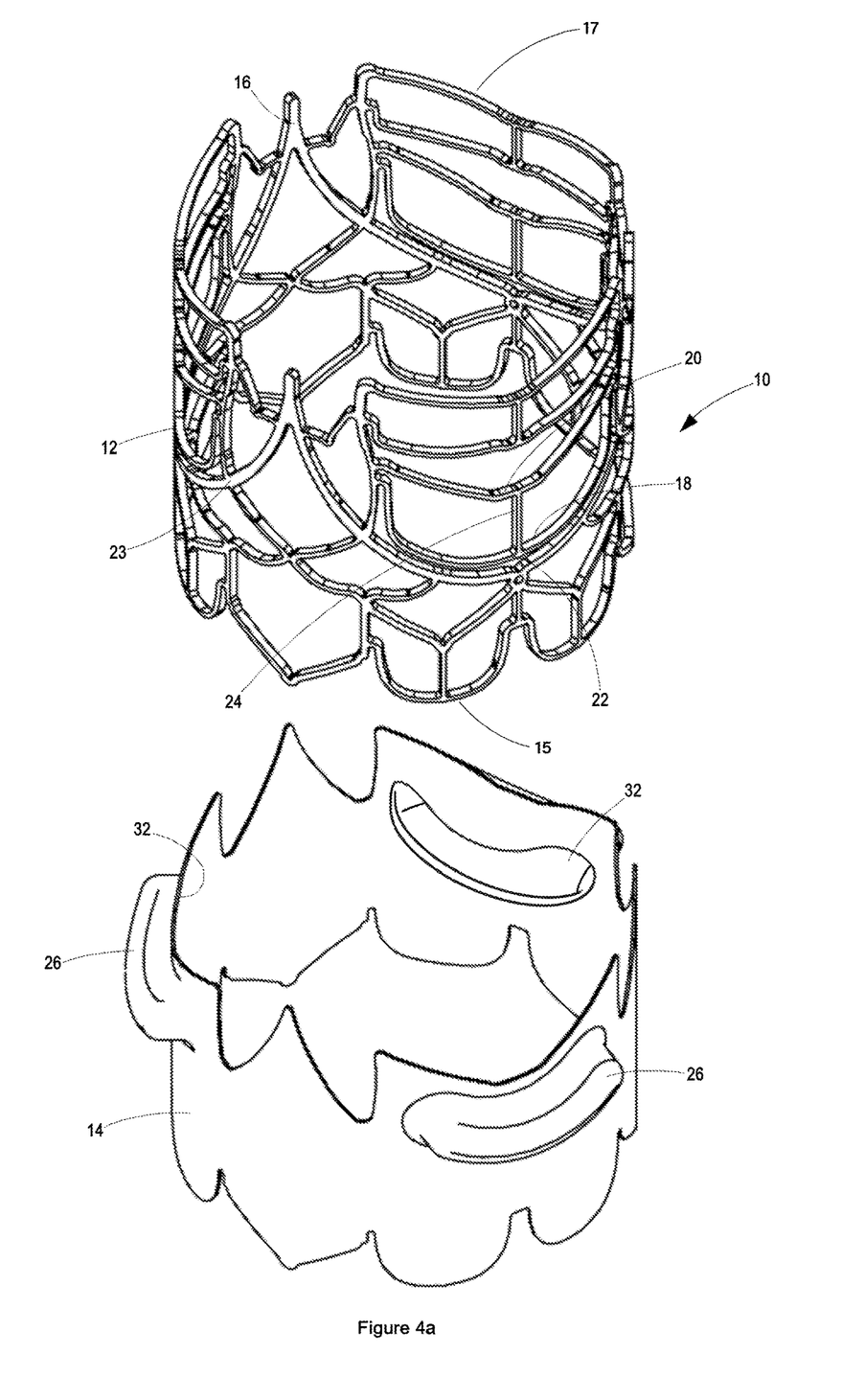
FIGS. 4a and 4b are exploded perspective views of the expandable sleeved stent in FIG. 1, in a nascent condition.
Figure 4B:
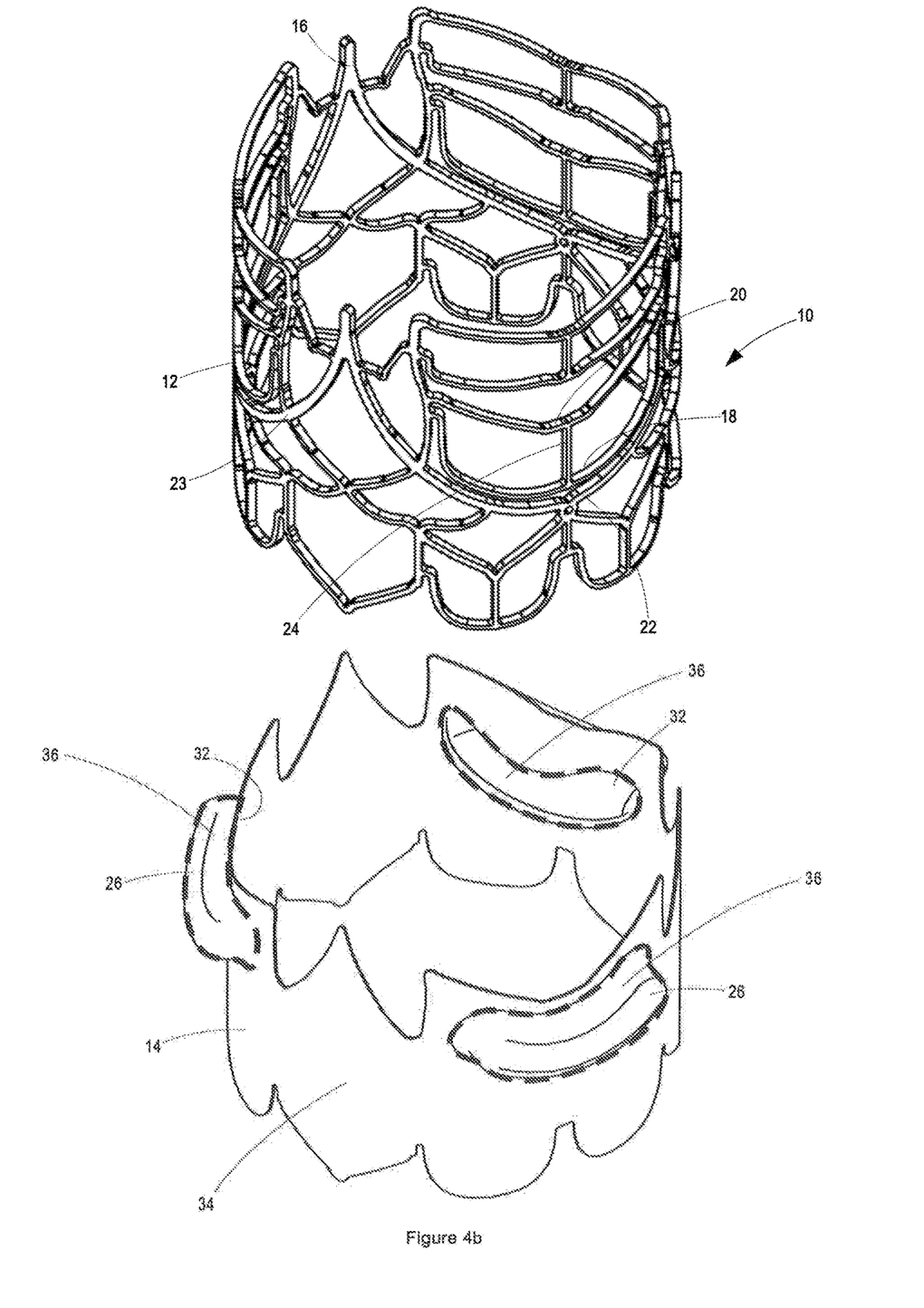
Figure 5:
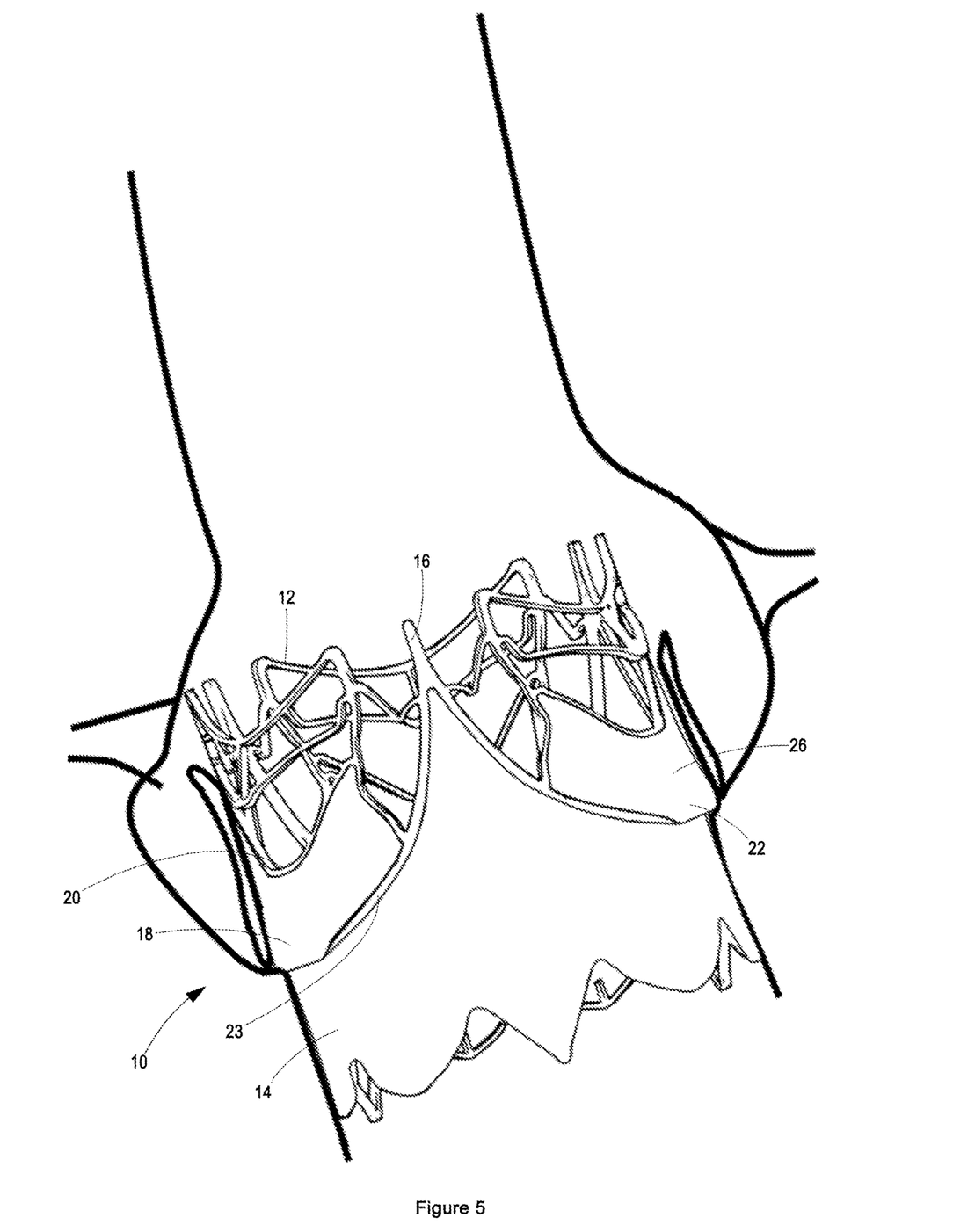
FIG. 5 is a side view of the expandable sleeved stent in FIG. 1 in an expanded condition, with the expandable sleeved stent located within an aortic root.

The stent 12 is a tubular body that is laser cut from a single right circular cylindrical tube (typically between 18 mm and 30 mm in outer diameter) to integrally form a latticed peripheral wall 16 having first and second axial ends 15, 17 and arms 18. Preferably, the stent 12 is coated with a polymer. FIG. 4a shows the stent 12 in a nascent condition (i.e. after being laser-cut, but before being crimped).

Figure 1:
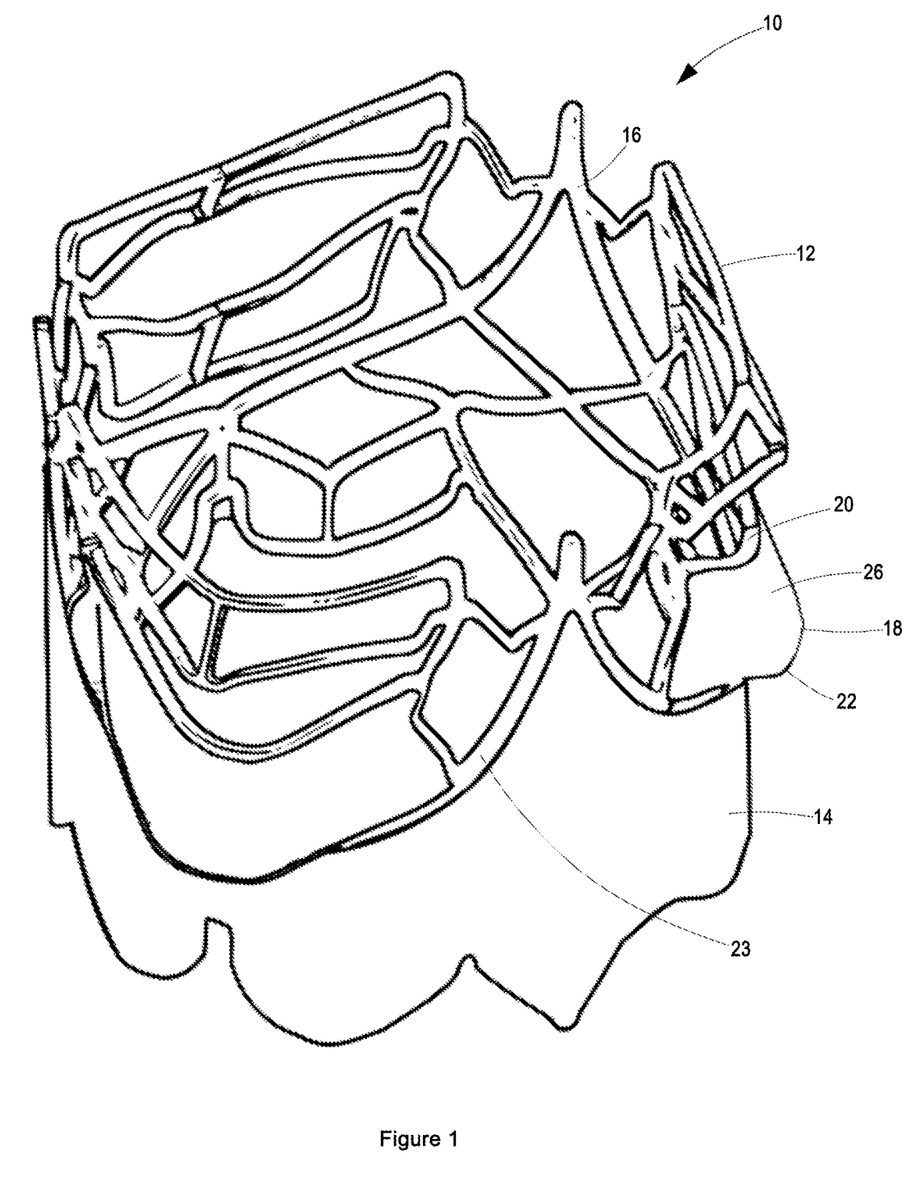
FIG. 1 is a perspective view of an expandable sleeved stent according to a preferred embodiment of first and second aspects of the invention, with the sleeved stent in an expanded condition.
Figure 2:
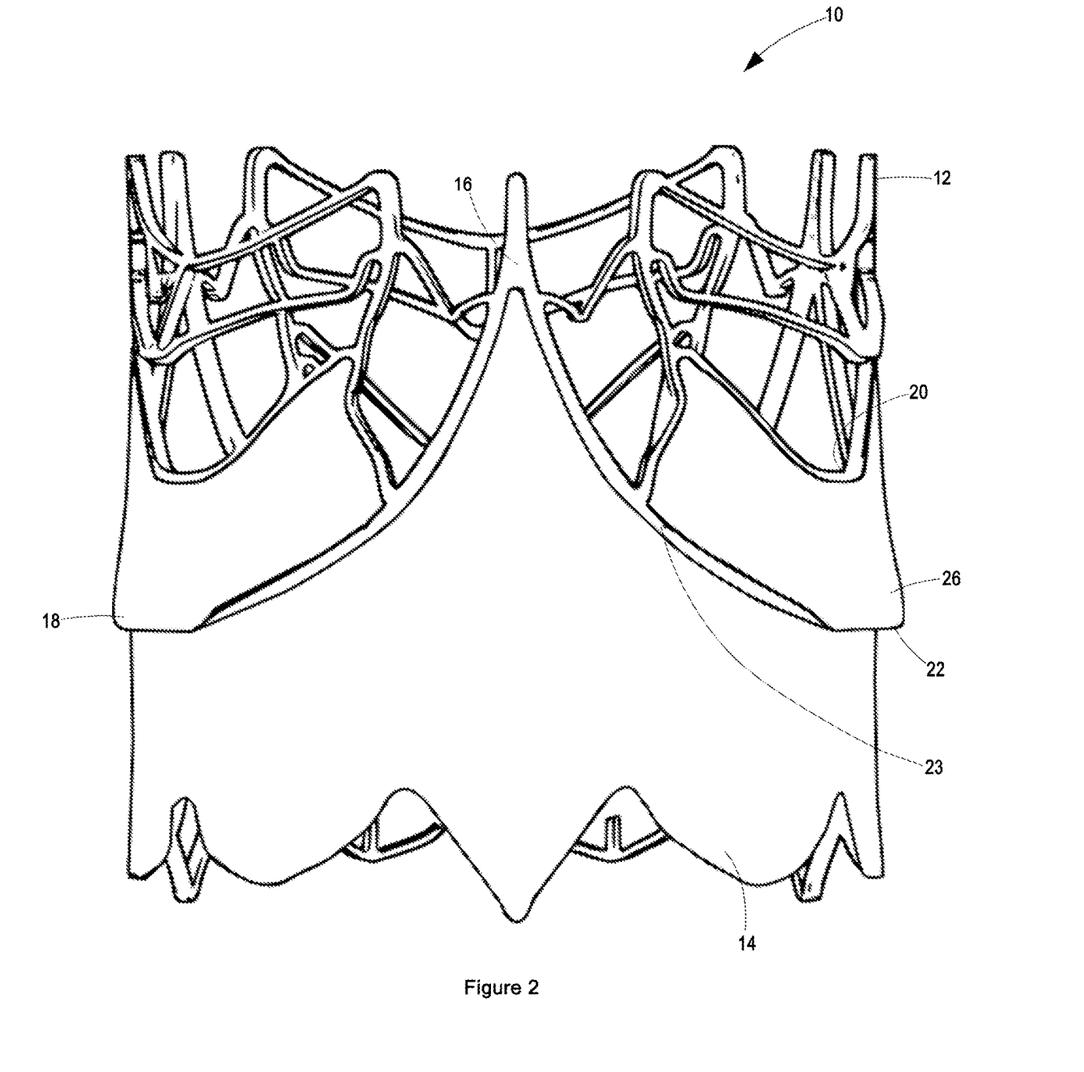
FIG. 2 is a side view of the expandable sleeved stent in FIG. 1, in an expanded condition.
Figure 3:
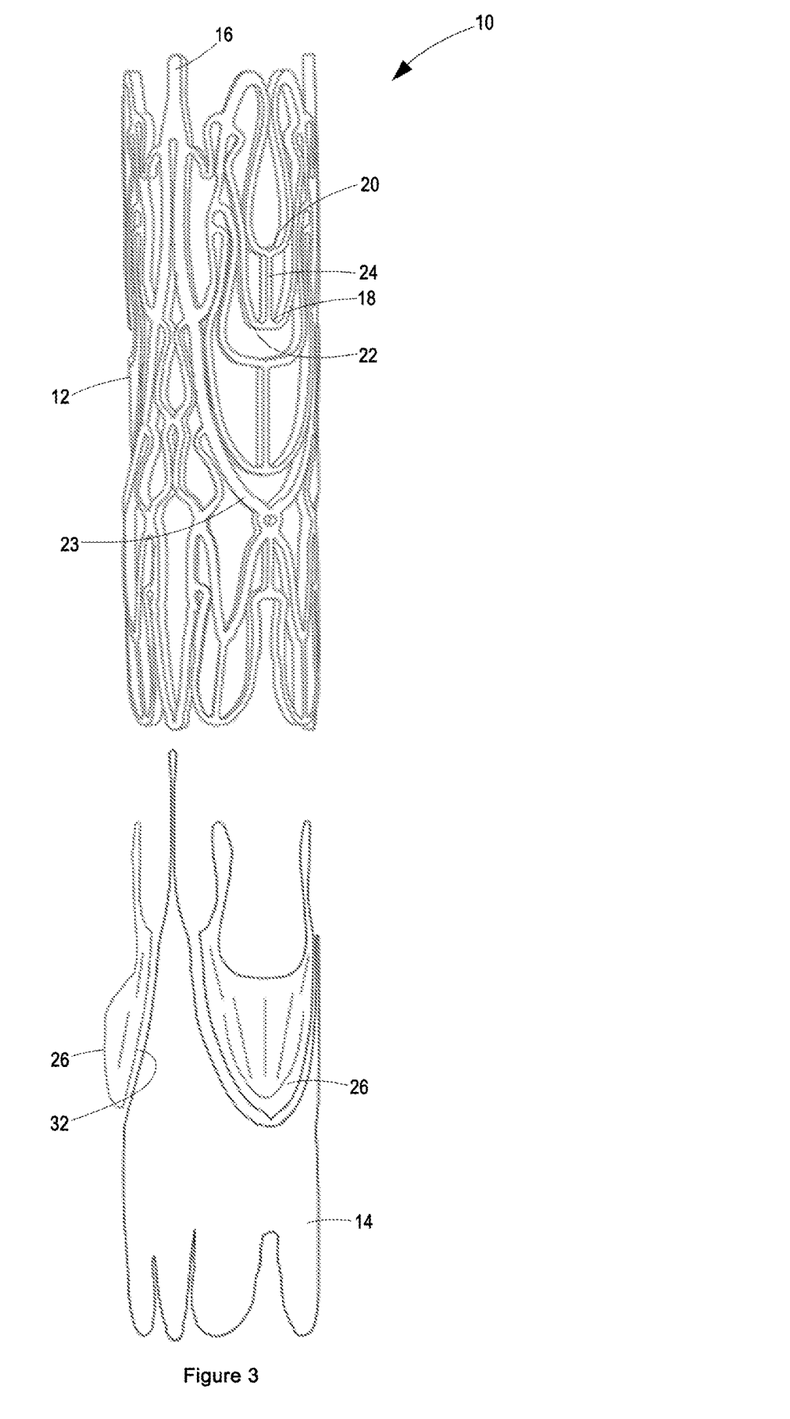
FIG. 3 is an exploded perspective view of the expandable sleeved stent in FIG. 1, in a crimped condition.

The latticed peripheral wall 16 permits the stent 12 to be: crimped (i.e. radially compressed) under the influence of an enveloping external radially compressive force to a crimped condition shown in FIG. 3; and radially expanded under the influence of an internal radially expansive force to an expanded condition shown in FIG. 1.

Three arms 18 are symmetrically arranged about the stent 12. Each arm 18 comprises: a first arm lattice member 20; a generally U-shaped second arm lattice member 22; and a third arm lattice member 24 bridging the first and second arm lattice members 20 and 22.

The latticed peripheral wall 16 includes a scalloped member 23 adjacent each second arm lattice member 22 (i.e. neighbouring the second arm lattice member 22 in the direction towards the first axial end 15 of the stent 12 tubular body).

The stent 12 is described in more detail in co-pending patent application no. PCT/ZA2017/050025 (published as WO/2017/190161), which application is incorporated herein by reference.

Each arm 18 is hingedly movable relative to the latticed peripheral wall 16 between:
   an initial configuration (i.e. when the stent 12 tubular body is in the crimped condition) in which the arms 18 are aligned with the adjacent latticed peripheral wall 16; and
   a radially protruding configuration in which the arms 18 protrude radially from the adjacent latticed peripheral wall 16—the free ends of the arms 18 (i.e. the second arm lattice members 22) displaced radially outwards relative to the adjacent latticed peripheral wall 16.

Expansion of the stent 12 from the crimped condition to the expanded condition causes the arms 18 to move from the initial configuration towards the radially protruding configuration.

The sleeve 14 is generally right circular cylindrical in shape and defines three radially outwards extending humps 26.

Figure 6:
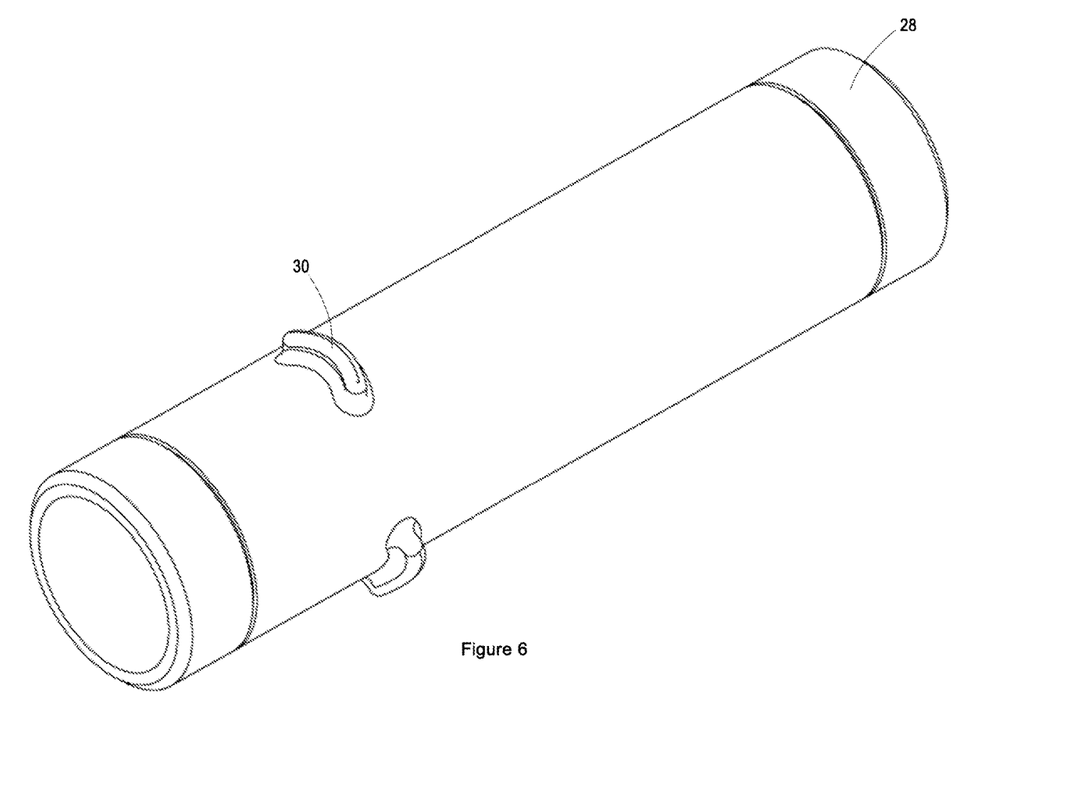
FIG. 6 is a perspective view of a second cylindrical mandrel used to form a sleeve forming part of the expandable sleeved stent in FIG. 1.

The sleeve 14 is formed by:
   electrospinning a polymer onto a first cylindrical mandrel (not shown);
   stretching the sleeve 14 over a second cylindrical mandrel 28 (shown in FIG. 6) that defines three radially outward extending kidney-shaped humps 30 symmetrically spaced about the second cylindrical mandrel 28; and
   heating the sleeve 14 to cause the sleeve 14 to assume the shape of the second cylindrical mandrel 28 (with kidney-shaped humps).

The sleeve 14 is placed over the stent 12 (when the stent 12 tubular body is in the nascent condition shown in FIG. 4a), with the humps 26 formed in the sleeve 14 radially overlying the stent 12 arms 18. More particularly, with reference to FIG. 4b, the sleeve 14:
   (i) in the region 34 (i.e. region outside the dashed lines) that radially overlaps the latticed peripheral wall 16 is right circular cylindrical in shape; and
   (ii) in the regions 36 (i.e. regions within the dashed lines) that radially overly the arms 18 define: (a) radially outward extending kidney-shaped humps 26 curving between the axial ends of the second arm lattice members 22; and (b) pockets 32 between the humps 26 and the corresponding arms 18.

The sleeve 14 is bonded to a first axial end 15 of the stent 12 tubular body, and extends from the first axial end 15 of the stent 12 tubular body, circumferentially covering at least a portion of the radial outer surface of the latticed peripheral wall 16 between the free ends of the arms 18 (i.e. the second arm lattice members 22) and the first axial end 15 of the stent 12 tubular body. The sleeve 14 further extends along the stent 12 tubular body to bridge the spaces between: the portions of the latticed peripheral wall 16 adjacent the arms 18; and the free ends of the arms 18 (i.e. the second arm lattice members 22). The sleeve 14 may be secured (i.e. bonded) to the free ends of the arms 18 (i.e. the second arm lattice members 22). Alternatively (as shown in the Figures), the sleeve 14 may be secured (i.e. bonded) to the first arm lattice members 20. Further alternatively, the sleeve 14 may extend beyond the arms 18 and be secured (i.e. bonded) to the stent 12 tubular body in the vicinity between the free ends of the arms 18 (i.e. the second arm lattice members 22) and the second axial end 17 of the stent 12 tubular body. Preferably, the sleeve 14 is also bonded to the scalloped members 23.

Since the stent 12 is coated in a polymer, the sleeve 14 can be bonded to the polymer coating 19 on the stent 12 to secure the sleeve 14 to the stent 12.

The stent 12 with sleeve 14 thereon is then crimped to a crimped condition shown in FIG. 3.

Upon radial expansion of the expandable sleeved stent 10:
   The stent 12 tubular body expands radially.
   The free ends of the arms 18 displace/protrude radially outwards from the adjacent latticed peripheral wall 16. Preferably, the free ends of the arms 18 (i.e. the second arm lattice members 22) are not secured (i.e. are not bonded) to the sleeve 14, such that protrusion of the arms 18 radially from the adjacent latticed peripheral wall 16 causes: (i) the free ends of the arms 18 (i.e. the second arm lattice member 22) to protrude into the pockets 32 defined by the sleeve 14 humps 26, sliding along the radial inner surface of the humps 26 defined by the sleeve 14; and (ii) the portions of the sleeve 14 that bridge the latticed peripheral wall 16 and the arms 18 to flare radially outwards.

When the stent 12 is in the expanded condition, the arms 18 provide support for the humps 26 defined by the sleeve 14, resisting radial inward collapse of the humps 26.

Although the sleeve 14 may be made of a single layered polymer material, portions of the sleeve 14 may be reinforced with a second polymer layer, in use, to withstand large surface areas of pressure differential across the sleeve 14.

Optionally, the expandable sleeved stent 10 includes a valve axially within the stent 12.

By extending the sleeve 14 from the first axial end 15 of the stent 12 beyond the free ends of the arms 18, the expandable sleeved stent 10 increases the sleeved axial length for stents 12 with radially expanding arms 18. Furthermore, by extending the arms 18 radially inwards of the sleeve 14 (i.e. within the humps 26 defined by the sleeve 14), the expandable sleeved stent 10 increases the axial cross-sectional area sealed by the sleeve 14. Even further, since the sleeve 14 in the vicinity of the humps 26 is expanded radially by the arms 18, the portions of the sleeve 14 that extend into sinuses (i.e. the humps 26) are mechanically supported in such radially extended condition by the radially protruding arms 18. Furthermore, since the sleeve 14 bridges the gap between the free ends of the arms 18 and the adjacent latticed peripheral wall 16, when viewed in axial cross-section in the vicinity of the humps 26, an effective continuous non-circular seal (i.e. with added humps/lobes formed thereby) is provided by the sleeve 14.

The combination of:
increasing the axial length of the sleeve 14 along the stent 12;
mechanically supporting the humps 26 defined by the sleeve 14 in a radially protruding condition;
bridging the gap between the free ends of the arms 18 and adjacent latticed peripheral wall 16; and
providing a continuous non-circular seal in axial cross-section (in the vicinity of the humps 26), renders the expandable sleeved stent 10 suited to address leakages (including paravalvular leakage) resulting from positioning and expanding the expandable sleeved stent 10: too low within the cardiovascular system; or adjacent a large sinus or aneurysm.

The invention claimed is:

1. An expandable sleeved stent comprising:
    a tubular body defined by a latticed peripheral wall having first and second axial ends and at least two arms that, upon radial expansion of the tubular body from a crimped condition to an expanded condition, protrude radially from the latticed peripheral wall, a free end of each arm being radially displaceable relative to the adjacent latticed peripheral wall;
    a sleeve that:
        extends from the first axial end of the tubular body and circumferentially covers at least a portion of a radial outer surface of the latticed peripheral wall between the free ends of the arms and the first axial end of the tubular body;
        bridges spaces between portions of the latticed peripheral wall adjacent the arms; and the free ends of the arms;
        is secured to either: (i) the arms; or (ii) the tubular body in a vicinity between the free ends of the arms and the second axial end of the tubular body;
        is right circular cylindrical in a region that radially overlaps the latticed peripheral wall; and
        defines humps radially overlying the arms such that, when the tubular body is in an uncrimped condition and the sleeve is secured to the tubular body, the humps define pockets between the humps and the corresponding arms,
    wherein, upon radial expansion of the tubular body from the crimped condition towards the expanded condition, the free ends of the arms protrude radially outwardly into the pockets to mechanically support the humps and to radially outwardly flare
    portions of the sleeve that bridge the latticed peripheral wall and the arms.

2. The expandable sleeved stent according to claim 1, wherein:
    each arm includes: (i) a first arm lattice member; (ii) a U-shaped second arm lattice member; and (iii) a third arm lattice member bridging the first and second arm lattice members; and
    the sleeve extends to, and is secured to the first arm lattice member of each arm.

3. The expandable sleeved stent according to claim 2, wherein, for each arm, the second arm lattice member is not secured to the sleeve, permitting sliding movement of the second arm lattice member along the hump.

4. The expandable sleeved stent according to claim 3, wherein the sleeve is made of an electrospun polymer.

5. The expandable sleeved stent according to claim 4, wherein the sleeve is bonded to the latticed peripheral wall.

6. The expandable sleeved stent according to claim 5, wherein the sleeve is bonded to scalloped members forming part of the latticed peripheral wall adjacent the second arm lattice members.

7. The expandable sleeved stent according to claim 6, wherein: the arms included in the tubular body limited to three in number; and the humps defined by the sleeve are limited to three in number.

* * * * *